United States Patent
Brilliant

[19]
[11] Patent Number: 5,885,075
[45] Date of Patent: Mar. 23, 1999

[54] ORTHODONTIC ARCH WIRE DISPENSER

[76] Inventor: Margo Kay Brilliant, 19390 NE. 22 Rd., North Miami Beach, Fla. 33179

[21] Appl. No.: 646,041

[22] Filed: May 7, 1996

[51] Int. Cl.[6] ............................... A61C 3/00; A47F 7/08; A47F 7/00
[52] U.S. Cl. ............................... 433/20; 211/33; 211/61; 211/163; 211/309; 211/312 C
[58] Field of Search ............................... 433/20; 211/33, 211/61, 27, 70, 163, 312 C, 309; 206/449, 820

[56] References Cited

U.S. PATENT DOCUMENTS

| B 91 | 1/1879 | Martin . | |
|---|---|---|---|
| 857,274 | 6/1907 | Gabasio . | |
| 1,774,195 | 1/1930 | Alland . | |
| 2,226,626 | 12/1940 | Mann | 312/71 |
| 2,918,167 | 12/1959 | Lowen | 206/42 |
| 3,207,564 | 9/1965 | Patrick | 312/73 |
| 3,212,670 | 10/1965 | Tint et al. | 221/312 |
| 3,693,806 | 9/1972 | Lit et al. | 221/70 |
| 4,170,325 | 10/1979 | Pawlowski et al. | 229/17 |
| 4,530,447 | 7/1985 | Greenspan | 221/288 |
| 4,643,334 | 2/1987 | Steele | 221/63 |
| 4,900,251 | 2/1990 | Andreasen | 433/20 |
| 5,063,082 | 11/1991 | Adel | 427/2 |

FOREIGN PATENT DOCUMENTS 736938  9/1932  France .

*Primary Examiner*—Nicholas D. Lucchesi
*Attorney, Agent, or Firm*—Robert M. Schwartz

[57] ABSTRACT

A dispenser and method for storing and dispensing orthodontic arch wires of arcuate configuration, having first and second pairs of opposed side walls of generally rectangular disposition closed by a bottom wall and an opposed top wall to store arch wires in a stacked relationship generally parallel to the first pair of side walls, the top wall having an opening at least slightly shorter than the base width of said arch wire, such that the arch wire will protrude only a distance from the dispenser sufficient to be grabbed and pulled when removed from the dispenser through said opening and the second pair of opposed side walls constructed and arranged to maintain the apex of the stored arch wire orientated toward the dispenser opening such that the arch wires can be dispensed without contaminating the remaining arch wires.

12 Claims, 3 Drawing Sheets

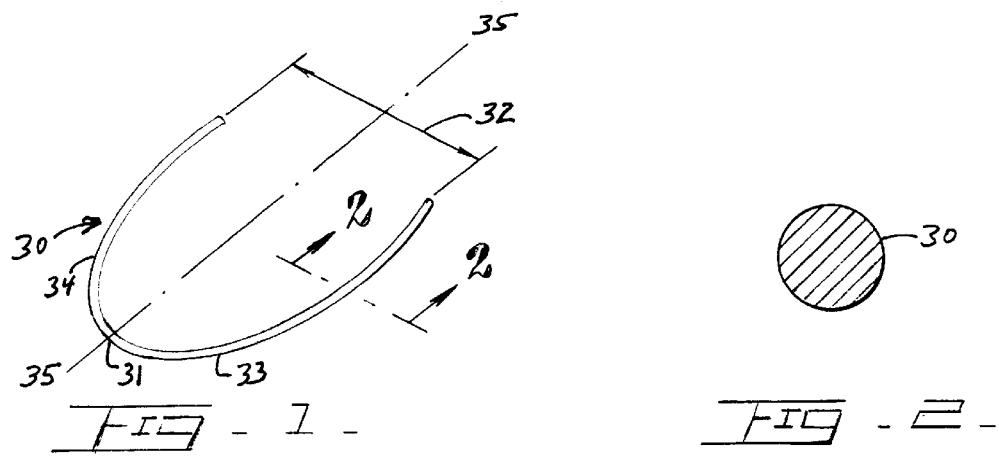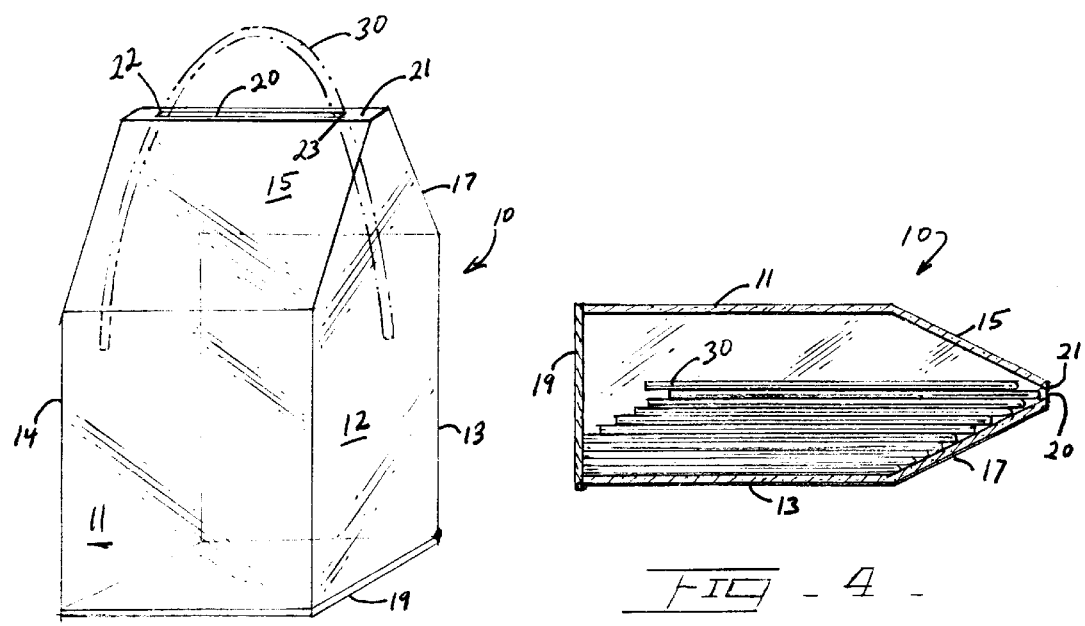

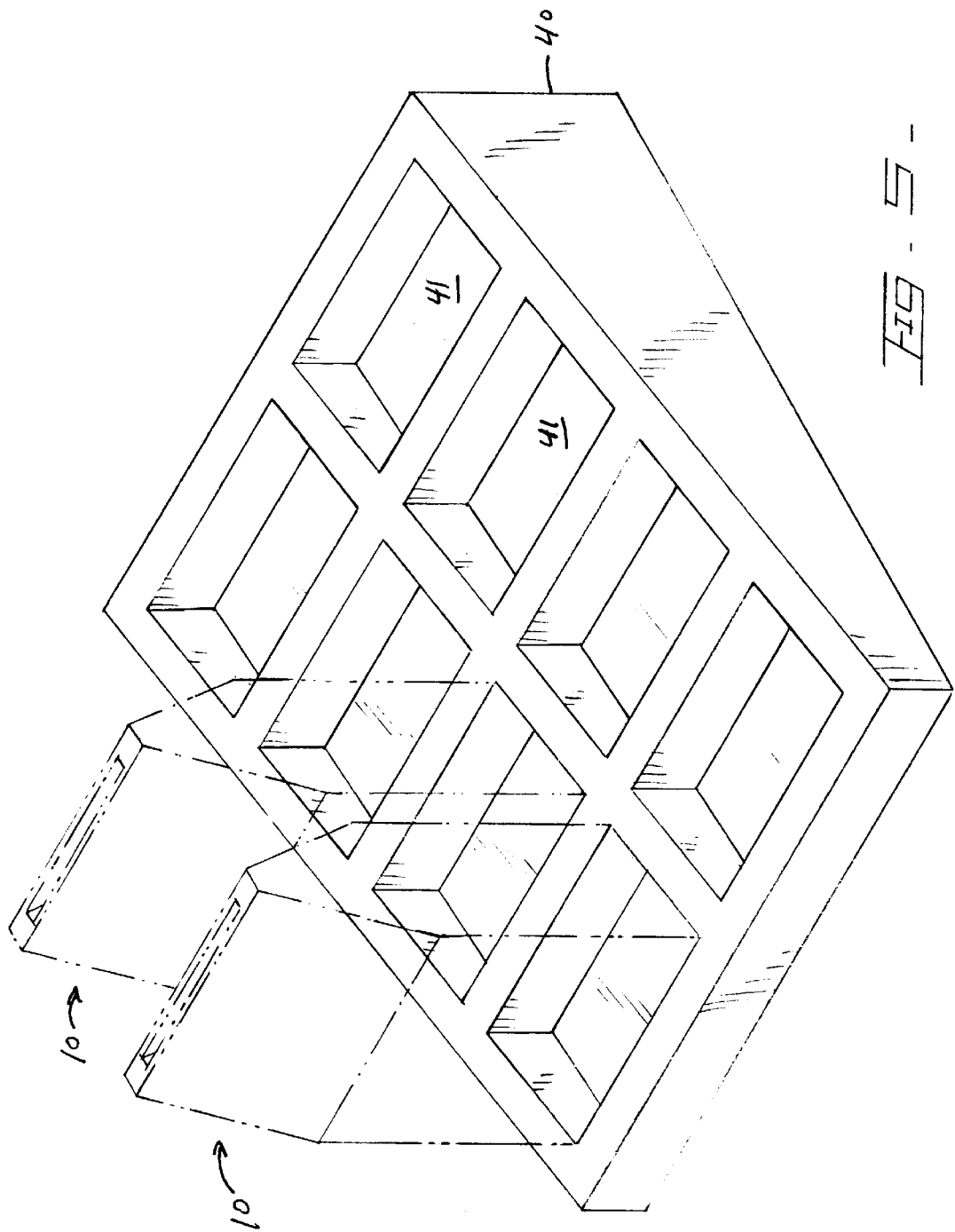

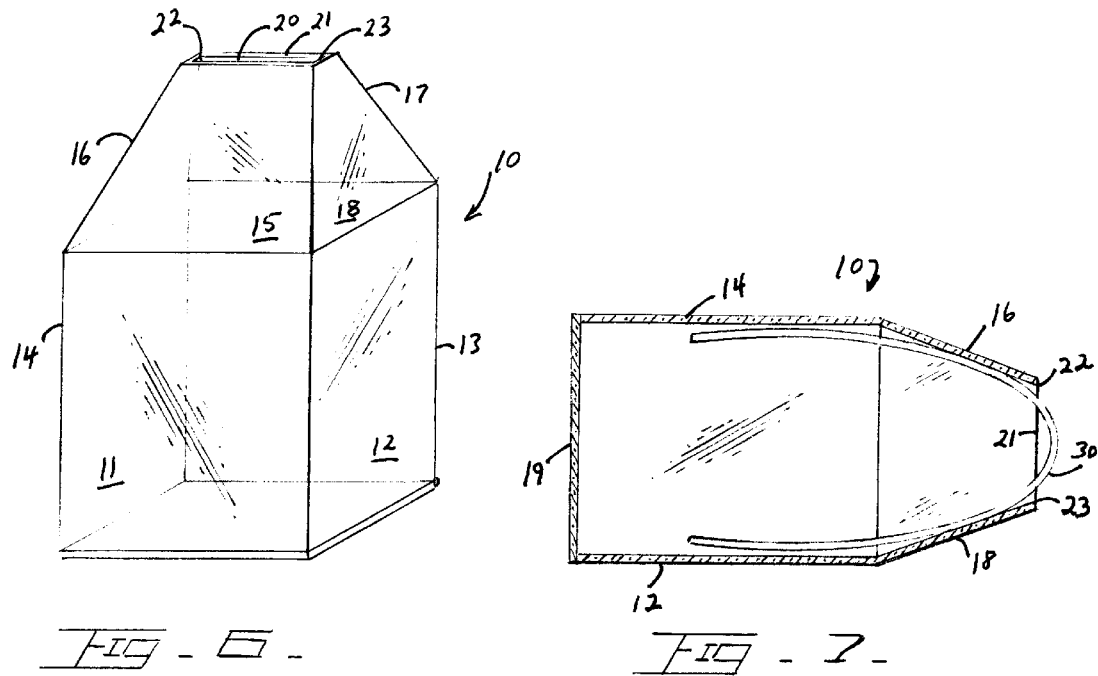
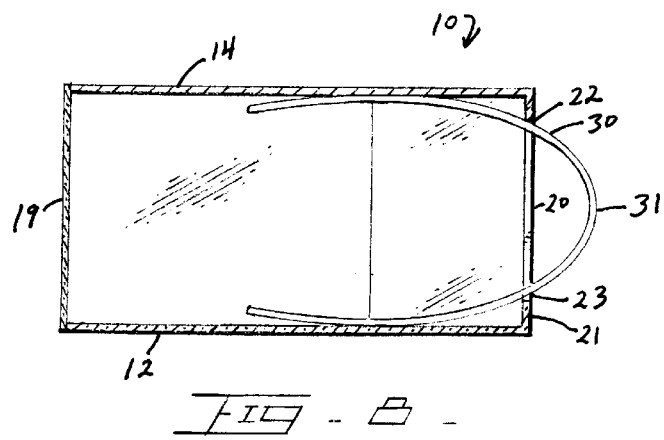

ORTHODONTIC ARCH WIRE DISPENSER

BACKGROUND OF THE INVENTION

This invention is used in the orthodontic dental field and, more particularly, is an arch wire dispenser and method to store and dispense orthodontic arch wires. Arch wires are generally U-shaped or parabolic shape, are formed of shape memory alloys and usually have a circular or rectangular cross section. In addition to the numerous cross sectional shapes, arch wires come in different shapes, sizes and strengths. They are an integral part of the orthodontic office treatment and are therefore kept at each chair side location in close proximity to the patient and within easy reach of the treating doctor or assistant (technician).

Arch wires usually come from a manufacturer in non-sterile packages, in groups of five to ten or twenty wires. In practice, the original packages are kept at the chair side location where the wires are removed from said packages or are organized and displayed in sets on racks or other displays visible to the technician. When an arch wire is needed, the treating technician selects the desired wire from the display rack. In the process of removing a wire from the rack, the remaining wires can and do become contaminated by the surrounding air, and by any contact between the hands or gloves of the technician and/or cross contamination from the patient either directly or indirectly as a result of the technician's contact with the patient. Likewise, when the wires are organized on a display rack, they come into contact with the ambient air or as previously stated, they come in contact with contamination from the technician or indirectly from another patient.

This invention prevents non-selected, remaining arch wires from becoming contaminated as will become obvious in the light of a description of the embodiment of this invention that follow.

Applicant conducted a patent novelty search. The following prior art patents were found, but do not disclose the novel dispenser system of the present invention.

French Patent No. 736,938 patented May 11, 1932 discloses means for dispensing pointed projectiles, possibly pencils, but with no means to limit their free fall from an apertured opening.

U.S. Pat. No. 857,274 to Gabasio, issued Jun. 18, 1907, discloses a match box dispenser for delivering a few matches at a time as opposed to the present invention only delivers a single device. Further, this patent discloses side flanges N are used to direct the dispensed article, but that do not control the orientation of the dispensed article.

What appears to be U.S. Patent to Martin, that appears in hand writings on the document to have issued Jan. 9, 1879, discloses a similar device as disclosed by Gabasio.

U.S. Pat. No. 1,744,195 to Alland, patented Jan. 21, 1930 discloses a cigarette dispenser to discharge stored cigarettes which completely drop from the container by gravity.

U.S. Pat. No. 2,226,626 to Mann, patented Dec. 31, 1940 discloses a cracker dispenser where crackers are horizontally placed in tiers. Though the crackers may be removed one at a time without touching the others, more than one cracker is available for removal at a time through opening 17, and thus contamination of the remaining crackers is not prevented.

U.S. Pat. No. 2,918,167 to Lowen, patented Dec. 19, 1957, discloses a pill or tablet dispenser, which is a plug for insertion into a conventional container. The plug includes an inner passageway constructed and arranged to allow only a single pill or tablet to pass freely out of the dispenser.

U.S. Pat. No. 3,207,564, issued to Patrick et al., patented Sep. 21, 1965 discloses a wire dispenser where the wires are stored in tubular containers, such that several wires within the tubular container are exposed and all are touched when removed from opening from the exposed end through aperture slot 46.

U.S. Pat. No. 3,212,670 issued to Tint et al., patented Oct. 19, 1965 recognizes the need of dispensing sterile prepackaged medical devices without affecting the sterility of the other needles remaining in the package. However, Tint's device dispenses round needles from a tubular bodied container, and, therefore, does not deal with the problems of dispensing flat objects.

U.S. Pat. No. 3,693,806 to Lit et al., patented Sep. 26, 1972 discloses a rotatable dispenser including a pair of disks, which has a large capacity for different kinds of materials to dispense bundles of precut lengths of wire from a single dispenser.

U.S. Pat. No. 4,170,325 to Pawlowski et al., patented Oct. 9, 1979 discloses a dispensing carton of articles to be stacked in an array and assuming an angular disposition within the carton.

U.S. Pat. No. 4,530,447 to Greenspan, patented Jul. 23, 1985 discloses a device to dispense a pill through a pair of juxtaposed openings.

U.S. Pat. No. 4,643,334 to Steele, patented Feb. 17, 1987 discloses a gravity-fed dispenser where the weight of the stacked items to be dispensed forces the item through a dispensing aperture toward a hand-engageable position.

U.S. Pat. No. 4,900,251 to Andreasen, patented Feb. 13, 1990 discloses generally parabolic shaped arch wires having shaped memory alloys, but does not disclose or discuss means of storing and/or dispensing an arch wire.

U.S. Pat. No. 5,063,082 to Adell patented Nov. 5, 1991 discloses a generally U-shaped orthodontic arch wire of circular cross section, but does not disclose or discuss means of storing and/or dispensing an arch wire.

It is an object of the present invention to provide a dispensing device for storing orthodontic arch wires which will prevent contamination of the non-dispensed arch wires while dispensing an arch wire one at a time.

It is another object of the present invention to provide a dispenser holder to hold several dispensers chair side in an organized manner.

It is an object of this invention to provide a method of storing, distributing and then dispensing arch wires.

It is still another object of the present invention to provide a dispenser that is economical to manufacture and that is of simple construction.

SUMMARY OF THE INVENTION

The present invention comprises an arch wire dispenser system, a dispenser holder and a method of storing and dispensing arch wires. The arch wire dispenser stores a plurality of wires, and is constructed and arranged for dispensing a singular arch wire at a time, avoiding the problems of the prior art of contaminating arch wires other than the one to be selected. Each wire dispenser is loaded with the same characteristic arch wires as received preferably in a sealed package from the manufacture. Several wire dispensers, each holding a different arch wire, e.g. different size, thickness, shape or characteristic, are held in place on a ramped dispenser holder, which is located in close proximity to the technician and patient. Each technician can arrange the order of the dispenser holder as he or she prefers.

Additional dispenser holders of the same or different size can be used by a technician and kept in close proximity to the technician as they may prefer or as work dictates.

To retrieve an arch wire, the respective dispenser is located and removed from the dispenser holder. The dispenser is constructed and arranged such that a gentle shaking motion will cause a single arch wire to partially protrude from the dispenser, so that a technician can then remove the arch wire from the dispenser without contaminating the remaining arch wires which safely remain within the dispenser.

The dispenser is preferably made of inexpensive plastic or other such material and can be clear, opaque or solid. Manufacturers of arch wires may place their arch wires directly into the dispenser which then would be received by the orthodontist for placement into the dispenser holder. The dispenser itself is of nominal expense in comparison to the arch wires. Thus the manufacturer can place its name on the dispenser as well as size and characteristic information relating to the arch wire itself. The dispenser opening, where the arch wire is removed, of sufficient width to allow an arch wire to protrude from the dispenser with minimal effort, yet still of sufficient height to be tight enough against the arch wire to keep impurities out and prevent contamination. A single flap or a pair of flexible flaps (not shown) may also be used to prevent impurities from entering the dispenser opening. In an alternative embodiment, the dispenser rests in the dispenser holder with the dispenser opening oriented towards the bottom of the dispenser holder instead of upward away from the dispenser holder as shown.

DESCRIPTION OF THE DRAWINGS

In the drawings that form a part of the description of a preferred embodiment of this invention and wherein like reference numbers refer to like structural elements.

FIG. 1 is a perspective view of a typical arch wire.

FIG. 2 is a cross section of the arch wire of FIG. 1.

FIG. 3 is a perspective view of a dispenser of the present invention, showing in phantom a single arch wire partially protruding from the dispenser.

FIG. 4 is a side view in section of the dispenser shown in FIG. 3, with several arch wires therein.

FIG. 5 is a perspective view of a dispenser holder having the capacity of holding eight dispensers and showing two said dispensers in phantom.

FIG. 6 is an alternative embodiment of the present invention, similar to FIG. 3, where side walls 12 and 14 have upper flanged portions 16 and 18 respectively.

FIG. 7 is a side sectional view of the dispenser of FIG. 6 showing a dispensed arch wire protruding from the dispenser opening.

FIG. 8 is a side sectional view similar to that of FIG. 7, of the dispenser of FIG. 3 showing a dispensed arch wire protruding from the dispenser opening.

DESCRIPTION OF ILLUSTRATIVE PREFERRED EMBODIMENTS

Dispenser 10, as seen in FIG. 3, includes a first pair of side walls 11 and 13, and a second pair of opposed side walls 12 and 14. Dispenser 10 includes a bottom wall portion 19, an opposed top wall 21 and a dispenser opening 20 formed in said top wall 21. Two of said side walls 11 and 13 include an obliquely upwardly extending side flange portion 15 and 17, respectively. Top wall 21 interconnects the upper ends of side flange portions 15 and 17. Dispenser opening 20 is rectangular, having a width oriented along the lengthwise portion of said top wall 21. The width of dispenser opening 20 is slightly smaller than the width of an arch wire 30, and the height of said opening 20, oriented along the shorter portion of said top wall 21 is just slightly larger than the thickness of an arch wire 30. The latter is constructed of an arcuate shape that includes an apex or protruding mid-point 31, and is made of a flexible material such as spring metal.

Bottom wall portion 19 may be constructed and arranged to open reclose to allow either the manufacturer or the technician to add or remove arch wires as needed.

The width of side walls 11 and 13 and side walls 12 and 14 relative to the axial length and width of arch wires 30 will limit stored arch wires 30 from rotating or otherwise shifting within dispenser 10. As shown in FIG. 4, walls 11 and 13 and flange portions 15 and 17 will keep arch wires 30 substantially parallel to the plane of walls 11 and 13, likewise as shown in FIG. 7 walls 12 and 14 and flange portions 16 and 18 or as shown in FIG. 8 walls 12 and 14 will limit any rotation of central axis 35 of an arch wire 30 relative to the plane of walls 12 and 14, so that the region of midpoint 31 of each arch wire 30 will first protrude from opening 20 and the stored arch wires 30 will remain in substantial stacked relationship.

Dispenser opening 20 is constructed and arranged such that the central portion 31 of arch wire 30 will protrude only a sufficient distance through opening 20 so that a technician when dispensing an arch wire can remove said arch wire 30 by hand or an instrument, e.g. pliers. The length of opening 20 is less than the base width 32 of arch wire 30, such that arch wire 30 cannot freely slide out of dispenser 20 unless it is pulled, since the upper side portions, generally at 33 and 34 of arch wire 30 will engage opposite end portions edge 22 and edge 23 of dispenser opening 20.

An alternative embodiment of dispenser 10 is shown in FIGS. 6 and 7, where side walls 12 and 14 include upper flanged portions 16 and 18 respectively. In this embodiment, the overall length of dispenser opening 20 is the same as in the embodiment illustrated in FIGS. 3 and 8, but the length of top wall 21 is not as long as in FIGS. 3 and 8. In this embodiment, upper flanged portions 16 and 18 and edges 22 and 23 will come in contact with upper side portions 33 and 34 of arch wire 30 permitting the protrusion of arch wire 30 a distance but restricting the ejection of arch wire 30 from dispenser 10 until the arch wire 30 is removed by hand or with an instrument as described above.

In use, the technician gently shakes dispenser 10 to urge an arch wire 30 through the dispenser opening 20. As can be seen in FIGS. 7 and 8, an arch wire 30 protrudes from dispenser opening 20 a sufficient distance to enable a technician to grab its central portion for removal.

FIG. 5 shows a dispenser holder 40 having eight recessed storage compartments 41, for receiving and securely holding up to eight dispensers. Said holder 40 is constructed and arranged in a step ramp such that each dispenser can be easily seen by the technician. Depending on the scope of the user's practice, one of several dispenser holders of the same or different size can be used by the technician when conveniently placed preferably at chair side or other convenient location. However the dispensers are interchangeable, in that compartment 23 is made of a size complementary to that of dispenser 10.

A manufacturer of arch wires will now be able to pre-package arch wires of similar characteristics in each dispenser and offer their product line of arch wires in separate prepackaged dispensers to be held and stored in the dispenser holders and then used by the technician at chair side in the manner as described herein. The dispensers and holder or holders can further be arranged in numerous combinations to accommodate the practice and style of each technician.

Conforming to the provisions of the patent statutes, application has provided an explanation of the principle, preferred construction and mode of operation of this invention and has illustrated and described what is now considered to be its best embodiment. It is understood, however, that within the scope of the claimed subject matter that follows, the invention may be practiced otherwise than as specifically illustrated and described.

I claim:

1. A dispenser for storing and dispensing shaped, flexible orthodontic arch wires of arcuate configuration, said dispenser comprising first and second pairs of opposed side walls closed by a bottom wall and an opposed top wall constructed and arranged to store said arch wires orientated in the same plane as said first pair of side walls, said top wall having a means for dispensing a single arcuate arch wire at a time there through, said means comprising an opening in said top wall.

2. A dispenser as in claim 1 wherein said opening in said top wall is at least slightly shorter than the base width of said arch wire, such that said arch wire will protrude only a distance from said dispenser sufficient to be grabbed and pulled when removed from said dispenser through said opening.

3. A dispenser as in claim 1 wherein said second pair of opposed side walls are constructed and arranged to maintain the apex of each said stored arch wire orientated toward said dispenser opening.

4. A dispenser for storing and dispensing shaped, flexible orthodontic arch wires of arcuate configuration, said dispenser comprising first and second pairs of opposed side walls of generally rectangular disposition closed by a bottom wall and an opposed top wall constructed and arranged to store said arch wires in a stacked relationship generally parallel to said first pair of side walls, said first pair of side walls having upper portions connected to said top wall, said top wall having a means for dispensing a single arcuate arch wire at a time there though, said means comprising an opening adapted to be at least slightly shorter than the base width of one of said arch wires, such that an arch wire will protrude only a distance from said dispenser sufficient to be grabbed and pulled when removed from said dispenser through said opening.

5. A dispenser as in claim 4 wherein said second pair of opposed side walls have upper flanged portions connected to said top wall.

6. A dispenser as in claim 4 wherein said second pair of opposed side walls are constructed and arranged to maintain the apex of each said stored arch wire orientated toward said dispenser opening.

7. A dispenser as in claim 1 wherein said second pair of opposed side walls and said upper flanged portions connected to said second pair of side walls are constructed and arranged to maintain the midpoints of said stored arch wires orientated toward said dispenser opening.

8. A dispenser as in claim 1 further comprising a dispenser holder having a plurality of dispenser openings for supporting said dispenser.

9. A dispenser as in claim 8, wherein said dispenser holder has a plurality of storage compartments and said dispenser is one of a plurality of identical dispensers, each of said storage compartments being constructed and arranged to have a size complementary to that of a corresponding of said identical dispensers.

10. A method of storing and dispensing shaped, flexible orthodontic arch wires of arcuate configuration in a dispenser comprising first and second pairs of opposed side walls of generally rectangular disposition closed by a bottom wall and an opposed top wall constructed and arranged to store said arch wires in a stacked relationship parallel to said first pair of side walls, and said first pair of side walls having upper portions connected to said top wall, and said top wall having an opening at least slightly shorter than the base width of said arch wire, shaking said dispenser such that said arch wire protrudes only a distance from said dispenser sufficient to be grabbed and pulled when removed from said dispenser through said opening.

11. A method of storing and dispensing shaped, flexible orthodontic arch wires as in claim 10, wherein prior to dispensing, a plurality of arch wires having similar characteristics are stored in said dispenser.

12. A method of storing and dispensing shaped, flexible orthodontic arch wires as in claim 11, wherein one or more of said dispensers are held in a dispenser holder at a convenient chair side location, said dispenser holder having a plurality of storage compartments being constructed and arranged to have a size complementary to that of a corresponding of said identical dispensers.

* * * * *